United States Patent [19]

Katsuragawa et al.

[11] 4,302,306
[45] Nov. 24, 1981

[54] BROMINATION OF SIDE CHAIN OF M-PHENOXYTOLUENE

[75] Inventors: Kanzi Katsuragawa; Hideo Sakka; Keiichi Kihara, all of Shin-nanyo, Japan

[73] Assignee: Toyo Soda Manufacturing Co., Ltd., Shin-nanyo, Japan

[21] Appl. No.: 141,354

[22] Filed: Apr. 18, 1980

[30] Foreign Application Priority Data

May 31, 1979 [JP] Japan ................................ 54-66801

[51] Int. Cl.$^3$ ............................................. C07C 41/22
[52] U.S. Cl. ........................... 204/158 HA; 568/639; 204/163 R
[58] Field of Search ................... 570/196; 568/639; 204/158 HA, 163 R

[56] References Cited

U.S. PATENT DOCUMENTS 3,190,825  6/1965  Huyser ................................ 570/196
4,010,087  3/1977  Wood et al. ................. 204/158 HA
4,014,940  3/1977  Ume et al.

*Primary Examiner*—Bernard Helfin
*Attorney, Agent, or Firm*—Oblon, Fisher, Spivak, McClelland & Maier

[57] ABSTRACT

A process for brominating m-phenoxytoluene with a polyhaloethane having the formula

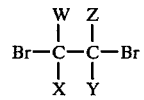

wherein W and Z respectively represent Cl or Br and X and Y respectively represent Cl, Br or H in a liquid phase.

6 Claims, No Drawings

BROMINATION OF SIDE CHAIN OF M-PHENOXYTOLUENE

BACKGROUND OF THE INVENTION

The present invention relates to a bromination of the side chain of m-phenoxytoluene by using a polyhaloethane as a brominating agent.

m-Phenoxybenzylbromide and m-phenoxybenzylidenedibromide obtained by a bromination of the side chain of m-phenoxytoluene are important intermediates for syntheses of synthetic pyrethroid type insecticides which have been recently found.

It has been reported that a bromination of the phenyl nucleus is resulted together with the bromination of the side chain of m-phenoxytoluene by using bromine as the brominating agent in the bromination of the side chain of m-phenoxytoluene.

The by-product of a phenyl nucleus brominated substituent causes a lower yield and trouble in industrial production because of the difficulty of a separation from the object side chain brominated product.

In order to decrease a production of the phenyl nucleus brominated substituent, it has been proposed to carry out the bromination of the side chain of m-phenoxytoluene with bromine at higher than 220° C. in the presence of phosphorus halides as disclosed in U.S. Pat. No. 4,014,940 and to carry out the bromination at higher than 180° C. under irradiation of ultraviolet rays as disclosed in U.S. Pat. No. 4,010,087. These processes are effective for decreasing the production of the by-product of the phenyl nucleus brominated substituent, but are not satisfactory since several % of the by-product is produced.

SUMMARY OF THE INVENTION

It is an object of the present invention to provide a selective bromination of the side chain of m-phenoxytoluene by reacting a bromine compound with m-phenoxytoluene without a production of a by-product formed by substituting bromine atom on the phenyl nucleus which is difficult to separate from the object product.

The foregoing and other objects of the present invention have been attained by a bromination of the side chain of m-phenoxytoluene by brominating m-phenoxytoluene with a polyhaloethane having the formula $$\begin{array}{c} W\quad Z \\ |\quad\ | \\ Br-C-C-Br \\ |\quad\ | \\ X\quad Y \end{array}$$

wherein W and Z respectively represent Cl or Br and X and Y respectively represent Cl, Br or H, as a brominating agent in a liquid phase in the presence or absence of water.

DESCRIPTION OF THE PREFERRED EMBODIMENTS

In accordance with the bromination of the present invention, hydrogen bromide and polyhaloethylene having the formula $$\begin{array}{c} W\quad Z \\ |\quad\ | \\ C=C \\ |\quad\ | \\ X\quad Y \end{array}$$

(bromine atoms are removed from the polyhaloethane) are simultaneously produced. The reaction is as follows.

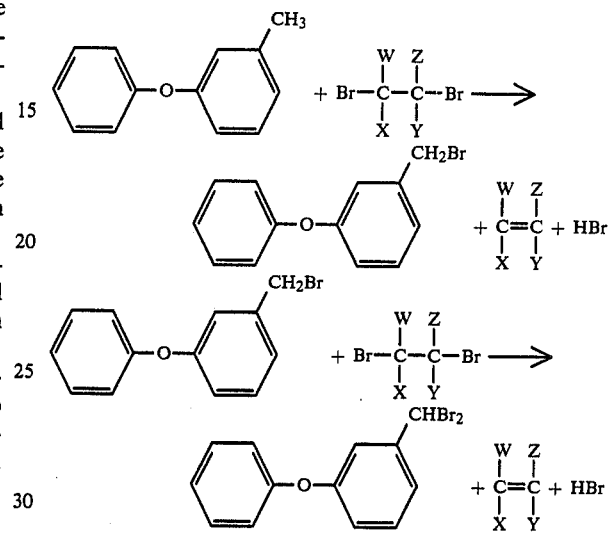

Suitable polyhaloethanes include 1,2-dibromotetrachloroethane, 1,2-dibromotrichloroethane, 1,1,2,2-tetrabromoethane, pentabromoethane, 1,2-dibromo-1,2-dichloroethane, etc.

The polyhaloethanes can be obtained by adding bromine to polyhaloethylene. Therefore, polyhaloethylene produced by the bromination of the side chain of m-phenoxytoluene can be reused by adding bromine to it to produce the polyhaloethane. The polyhaloethylene is easily available in an industrial scale and can be used as an economical bromine carrier.

When the bromination of the side chain of m-phenoxytoluene is carried out by using the polyhaloethane, only side chain is selectively brominated to obtain the object m-phenoxybenzylbromide and m-phenoxybenzylidenedibromide at high yield.

When a radical initiator is used for the reaction, the reaction is accelerated. When ultraviolet rays are irradiated instead of the radical initiator, the reaction is also accelerated. In the following description, the term of the use of the radical initiator means to include the irradiation of the ultraviolet rays.

The reaction is not performed at lower than 60° C. even though a radical initiator is used. When the radical initiator is used at higher than 60° C., the bromination of the side chain of m-phenoxytoluene is found. At a temperature of 60° to 70° C., the velocity of the bromination is slow and accordingly, it is preferable to perform the reaction at higher than 70° C. It is necessary to use a radical initiator at a temperature of lower than 150° C. in the bromination, however, it is unnecessary to use any radical initiator at a temperature of higher than 150° C. The velocity of the bromination is slow at a temperature from 150° C. to 180° C. without using a radical initiator and accordingly, it is preferable to accelerate the reaction by using a radical initiator. A radical initiator can be used at a temperature of higher than 180° C., though the bromination is performed at a desired velocity. When it is preferable to perform the reaction under the atmospheric pressure or lower, the temperature is preferable to be lower than the boiling point of m-phenoxytoluene. Therefore, the reaction temperature in the bromination without any radical initiator is in a range of 150° to 270° C. preferably 180° to 250° C.

Suitable radical initiators include the known radical initiators such as azobisisobutyronitrile and benzoyl peroxide and also ultraviolet rays.

The amount of azobisisobutyronitrile or benzoyl peroxide is higher than 0.5 wt. part preferably in a range of 1 to 100 wt. parts per 100 wt. parts of m-phenoxytoluene.

At a temperature for requiring the radical initiator, the rate of the bromination of m-phenoxytoluene can be controlled depending upon the amount of the radical initiator, since the bromination is stopped after consuming the radical initiator when the amount of the radical initiator is set.

An amount of the polyhaloethane should be greater than the stoichiometric equation and can be large excess. The reaction is accelerated and the yield is increased by using excess of the polyhaloethane. When the reaction is performed by using the radical initiator, the chain propagation of the radical reaction can be increased by using excess of the polyhaloethane so as to decrease the amount of the radical initiator.

However, excess of the polyhaloethane should be separated from the reaction product. Therefore, a desired excess amount of the polyhaloethane is in a range of 2 to 10 times the stoichiometric equation.

When excess of the polyhaloethane is used in the bromination, it is not preferable to use a solid polyhaloethane which is sublimated such as 1,2-dibromotetrachloroethane, but it is preferable to use a liquid polyhaloethane which is distilled under a reduced pressure such as 1,2-dibromotrichloroethane so as to be easily separable after the bromination. The recovered polyhaloethane can be reused for the bromination. It is preferable to incorporate a stabilizer which does not cause a trouble of the bromination of m-phenoxytoluene or the analogous diphenyl ether so as to prevent a decomposition of the polyhaloethane in the recovery by the distillation.

It is unnecessary to add a solvent in the bromination, though it is possible to use an inert solvent. The inert solvents are not reactive to the by-product of hydrogen bromide and do not prevent the radical reaction. Suitable inert solvents include halo-hydrocarbons such as carbon tetrachloride, 1,2-dichloroethane and aromatic solvents such as benzene, chlorobenzene, dichlorobenzene, dibromobenzene and diphenylether.

When water (which is not a solvent) is added, the bromination is accelerated and accordingly, the bromination can be performed at lower than 100° C. The reaction time can be shortened and the yield can be increased in comparison with the bromination in the absence of water.

The side chain brominated m-phenoxytoluene, and the m-phenoxytoluene and the polyhaloethane are substantially insoluble to water. When water is added, the organic phase is separated from the water phase.

It is especially effective to add water at a ratio of more than the amount of the by-product of hydrogen bromide by weight. The resulting hydrogen bromide can be collected in the reactor by dissolving hydrogen bromide into water.

When water is not added and hydrogen bromide is not discharged from the reactor, the bromination is performed under a higher pressure. When the bromination under the atmospheric pressure is preferable, the resulting hydrogen bromide is discharged from the reactor and is collected.

When the bromination is performed at a temperature higher than the boiling point of the resulting polyhaloethylene, the bromination can be performed under the atmospheric pressure by distilling and removing hydrogen bromide and the polyhaloethylene, whereby only the side chain brominated m-phenoxytoluene can be remained in the reactor. The same bromination can be performed under a reduced pressure.

The bromination of the present invention is selectively performed only for the side chain without the bromination of phenyl nucleus. In the side chain, the bromination is sequentially performed to proceed for production of m-phenoxybenzylbromide, m-phenoxybenzylidenedibromide, and m-phenoxybenzylidynetribromide in sequence. Thus, the selectivity to the object product in the sequential bromination is superior to those of the use of bromine. The selectivity can be increased by controlling the ratio of the bromination of m-phenoxytoluene.

When only m-phenoxybenzylbromide is desired as the product, the production of m-phenoxybenzylidenedibromide can be reduced to 1 to 2% by controlling the conversion of m-phenoxytoluene to lower than 80% preferably lower than 60%.

In accordance with the sequential bromination of the present invention, the bromination can be also applied for producing m-phenoxybenzylidenedibromide and m-phenoxybenzylidynetribromide from the reagent of m-phenoxybenzylbromide; or for producing m-phenoxybenzylidynetribromide from m-phenoxybenzylidenedibromide.

m-Phenoxybenzylbromide can be easily converted into m-phenoxybenzylacetate by an esterification with sodium acetate etc. in a solvent such as acetic acid. m-Phenoxybenzylacetate can be easily converted into m-phenoxybenzyl alcohol by a hydrolysis with a base in a solvent such as methanol.

The esterification and the hydrolysis are not disturbed even though the reagent of m-phenoxytoluene is incorporated.

In accordance with the above-mentioned treatments, m-phenoxybenzylidenedibromide is converted into m-phenoxybenzaldehyde. Therefore, when a mixture of m-phenoxybenzylbromide and m-phenoxybenzylidenedibromide is treated as mentioned above, m-phenoxybenzylacetate and m-phenoxybenzaldehyde are produced. From the mixture, m-phenoxybenzylacetate can be separated from m-phenoxybenzaldehyde by a distillation under a reduced pressure.

As described, in accordance with the present invention, the industrially available polyhaloethylene is used as a brominating agent to attain the selective bromination of the side chain without a production of the phenyl nucleus brominated substituent of m-phenoxytoluene which is not easily separated.

In accordance with the present invention, the economical production of m-phenoxybenzyl alcohol and m-phenoxybenzaldehyde is attained by using intermediates of the side chain brominated m-phenoxytoluene which can be obtained at high yield.

The present invention will be further illustrated by certain examples which are provided for purposes of illustration only and are not intended to be limiting the present invention.

EXAMPLE 1

Into a 100 ml. four necked flask equipped with a condenser, 18.4 g. (0.1 mole) of m-phenoxytoluene and 18.0 g. (0.055 mole) of 1,2-dibromotetrachloroethane were charged and heated with stirring. The reaction was continued until 1,2-dibromotetrachloroethane was not detected under a gas chromatography analysis of the reaction mixture.

The reaction temperatures and the integrated percents of the gas chromatography at reaction times are shown in Table 1.

TABLE 1

| Reaction time | 1 hr. 20 min. | 2 hr. 15 min. | 3 hr. 30 min. | 4 hr. 30 min. | 5 hr. 15 min. | 5 hr. 30 min. |
|---|---|---|---|---|---|---|
| Reaction temp. (°C.) | 130 | 150 | 170 | 190 | 200 | 200 |
| m-Phenoxytoluene (%) | 100 | 97.2 | 91.4 | 64.8 | 51.8 | 47.9 |
| m-Phenoxybenzylbromide (%) | | 2.8 | 8.6 | 33.5 | 46.2 | 50.0 |
| m-Phenoxybenzilidenedibromide (%) | | 0 | 0 | 1.7 | 2.0 | 2.8 |

At the reaction time of 5 hours 30 minutes, 1,2-dibromotetrachloroethane disappeared. The reaction was finished and the products were analyzed. The conversion of m-phenoxytoluene was 53.2%; and a selectivity to m-phenoxybenzylbromide based on m-phenoxytoluene was 93.4%. Any nucleus substituent was not found in any steps. The distilled products contained 8.7 g. of tetrachloroethylene and 4.5 g. of hydrogen bromide.

Condition of gas chromatography analysis.
Apparatus: GC-5A Shimazu Seisakusho K.K.
Packing:
Silicone DC-550 20%
Celite 545, 60/80 mesh
Column: Glass column having a diameter of 3 mm and a length of 2 m.
Condition for measurement:
Inlet temperature: 200° C.
Column temperature: 200° C.
Carrier gas: He 1.0 kg/cm$^2$

EXAMPLE 2

During 3 hours, 32 g. of bromine was added to 32 g. of trichloroethylene with stirring at a room temperature. Into the resulting solution, 9.6 g. of m-phenoxytoluene was added and the mixture was stirred at 210° C. for 1 hours 45 minutes.

The reaction mixture contained the unreacted 1,2-dibromotrichloroethane and 3.5 g. (selectivity: 26.6%) of m-phenoxybenzylbromide, and 12.5 g. (selectivity: 73.2%) of m-phenoxybenzylidenedibromide. A selectivity to m-phenoxybenzylbromide and m-phenoxybenzylidenedibromide base on m-phenoxytoluene was 99.8%. Any nuclear substituent was not found.

EXAMPLE 3

During 3 hours, 77 g. of bromine was added to 77 g. of trichloroethylene with stirring at a room temperature to obtain 1,2-dibromotrichloroethane which contains the unreacted trichloroethylene.

Into the resulting solution, 60 g. of m-phenoxytoluene was added and the mixture was stirred at 210° C. for 10 hours. After the reaction, 1,2-dibromotrichloroethane was not found in the reaction mixture, and the reaction mixture contained 34.7 g. (Selectivity: 40.4%) of m-phenoxybenzylbromide and 45.1 g. (Selectivity: 40.4%) of m-phenoxybenzylidenedibromide. Any nuclear substituent was not found in the reaction mixture.

For the purpose of reference there is provided hereinbelow an example of producing m-phenoxybenzaldehyde and m-phenoxybenzylalcohol using a reaction mixture solution containing these bromides.

Into the reaction mixture, 130 g. of acetic acid, 5 g. of water and 41.8 g. of sodium acetate were added and the mixture was stirred at 120° C. for 20 hours. After cooling the reaction mixture, 200 ml. of benzene was added and the product was extracted three times with 200 ml. of water to separate sodium acetate and the other water soluble materials. Benzene was distilled off from the benzene phase, and the residue was distilled under a reduced pressure of 1 mmHg. to obtain 24.4 g. of m-phenoxybenzaldehyde and 30.9 g. of m-phenoxybenzyl acetate.

Into m-phenoxybenzyl acetate, 150 g. of methanol was added and 150 g. of an aqueous solution of 95% methanol containing 7.0 g. of sodium hydroxide was added dropwise at a room temperature during 1 hour. The reaction mixture contained 25.0 g. of m-phenoxybenzyl alcohol. A selectivity to m-phenoxybenzaldehyde based on m-phenoxytoluene was 37.7% and a selectivity to m-phenoxybenzyl alcohol was 38.3%.

EXAMPLE 4

Into a 300 ml. photochemical reactor equipped with a refluxing condenser, 10 g. of m-phenoxytoluene, 8.6 g. of 1,2-dibromotetrachloroethane, and 100 g. of carbon tetrachloride were charged and the reactor was irradiated by a 100 W high pressure mercury discharge lamp (Rikokagaku Sangyo K.K.) and the mixture was stirred at the refluxing temperature of the solvent for 10 hours. The reaction mixture contained 5.5 g. of m-phenoxytoluene and 4.5 g. (Selectivity: 70.0%) of m-phenoxybenzylbromide. Any nucleus substituent was not found.

EXAMPLE 5

Into a 300 ml. photochemical reactor equipped with a refluxing condenser, 10 g. of m-phenoxytoluene, 8.6 g. of 1,2-dibromotetrachloroethane, 100 g. of carbon tetrachloride and 100 g. of water were charged and the reactor was irradiated by a 100 W high pressure mercury lamp and the mixture was stirred at the refluxing temperature of the solvent for 5 hours. The reaction mixture contained 5.0 g. of m-phenoxytoluene and 5.7 g. (Selectivity: 79.8%) of m-phenoxybenzylbromide. Any nucleus substituent was not found.

EXAMPLE 6

Into a 100 ml. four necked flask equipped with a refluxing condenser, 18.4 g. of m-phenoxytoluene, 40 g. of 1,2-dibromotrichloroethane, 40 g. of water and 1.0 g. of azobisisobutyronitrile were charged and the mixture was stirred under refluxing for 2 hours. The reaction mixture contained the unreacted 1,2-dibromotrichloroethane, 10.6 g. of m-phenoxytoluene and 10.9 g. of m-phenoxybenzylbromide. A selectivity to m-phenoxybenzylbromide was 98%. Any nuclear substituent was not found.

EXAMPLE 7

Into a 100 ml. four necked flask equipped with a refluxing condenser, 1.84 g. of m-phenoxytoluene, 6 g. of 1,2-dibromotetrachloroethane, 20 g. of bromobenzene, 20 g. of water and 0.4 g. of benzoyl peroxide were charged and the mixture was stirred at 100° C. for 4 hours. The unreacted 1,2-dibromotetrachloroethane was remained. According to a gas chromatography analysis (the same as Example 1), integrated percents of m-phenoxytoluene, m-phenoxy benzylbromide and m-phenoxybenzylidenedibromide were respectively 5.9%, 85.8% and 6.8%. Any nuclear substituent was not found.

EXAMPLE 8

Into a 100 ml. four necked flask equipped with a refluxing condenser, 1.84 g. m-phenoxytoluene, 10 g. of tetrabromoethane, 10 g. of water and 0.2 g. of benzoyl peroxide were charged and the mixture was stirred at the refluxing temperature for 3 hours. According to a gas chromatography analysis (the same as Example 1) of the organic phase separated from the reaction mixture, integrated percents of m-phenoxytoluene and m-phenoxybenzylbromide were respectively 51.5% and 48.5%. Any nucleus substituent was not found.

We claim:

1. A process for brominating the side chain of m-phenoxytoluene with a polyhaloethane having the formula

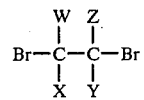

wherein W and Z respectively represent Cl or Br and X and Y respectively represent Cl, Br or H in a liquid phase.

2. A process according to claim 1 wherein said bromination is performed in the presence of a radical initiator or under irradiation of ultraviolet rays at higher than 60° C.

3. A process according to claim 1 wherein said bromination is performed in the absence of a radical initiator and ultraviolet rays at a reaction temperature of higher than 150° C.

4. A process according to claim 1, wherein said bromination is performed in the presence of water at a temperature lower than 100° C.

5. A process according to claim 1 wherein said polyhaloethane is produced by brominating a corresponding polyhaloethylene.

6. A process according to claim 1 wherein a stoichiometrical excess of said polyhaloethane is used in an inert solvent.

* * * * *